United States Patent [19]
Alker et al.

[11] Patent Number: 5,607,950
[45] Date of Patent: Mar. 4, 1997

[54] MUSCARINIC RECEPTOR ANTAGONISTS

[75] Inventors: David Alker, Birchington; Peter E. Cross, Canterbury; Alexander R. Mackenzie, Deal, all of England

[73] Assignee: Pfizer Inc., New York, N.Y.

[*] Notice: The term of this patent shall not extend beyond the expiration date of Pat. No. 5,422,358.

[21] Appl. No.: 195,888

[22] Filed: Feb. 10, 1994

Related U.S. Application Data

[63] Continuation of Ser. No. 890,596, filed as PCT/EP90/02041 Nov. 28, 1990, abandoned.

[30] Foreign Application Priority Data

Jan. 6, 1990 [GB] United Kingdom .................. 9000304

[51] Int. Cl.$^6$ .................. A61K 31/445; A61K 31/40; C07D 405/06; C07D 207/08
[52] U.S. Cl. .................. 514/320; 514/252; 514/255; 514/318; 514/321; 514/326; 514/340; 514/408; 514/422; 514/428; 544/336; 546/193; 546/196; 546/197; 546/213; 546/283.7; 546/284.1; 548/567; 548/568; 548/566
[58] Field of Search .................. 544/336; 548/567, 548/568, 566; 514/252, 255, 318, 320, 321, 326, 340, 408, 422, 428; 546/193, 196, 197, 213, 275

[56] References Cited

U.S. PATENT DOCUMENTS

| | | | |
|---|---|---|---|
| 4,810,713 | 3/1989 | Yanni et al. | 514/317 |
| 4,950,674 | 8/1990 | Yanni et al. | 514/317 |
| 5,070,087 | 12/1991 | Teng | 514/212 |
| 5,096,890 | 3/1992 | Cross | 514/422 |
| 5,233,053 | 8/1993 | Cross | 548/568 |

FOREIGN PATENT DOCUMENTS

| | | |
|---|---|---|
| 0178946 | 4/1986 | European Pat. Off. . |
| 0235463 | 9/1987 | European Pat. Off. . |

OTHER PUBLICATIONS

D. A. Walsh et al.: "Synthesis and anti–allergy activity of 4–(diarylhydroxy–methyl)–1–[3–(acryloxy)propylipiperidines] and structurally related compounds", Journal of Medicinal Chemistry, vol. 32, No. 1, Jan. 1989, American Chemical Society.

*Primary Examiner*—Ceila Chang
*Attorney, Agent, or Firm*—Peter C. Richardson; Paul H. Ginsburg; Garth C. Butterfield

[57] ABSTRACT

The invetion is a method of treating irritable bowel syndrome with a compound selected from the formula

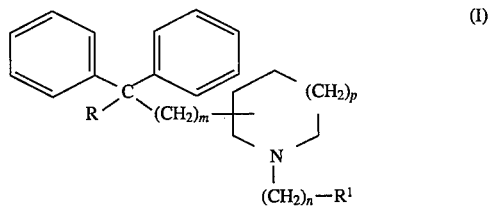

(I)

wherein R, R$^1$, m, n p are as defined in the specification, or a pharmaceutically acceptable salt thereof.

5 Claims, No Drawings

MUSCARINIC RECEPTOR ANTAGONISTS

This is a continuation of application Ser. No. 07/890,596, filed as PCT/EP90/02041 Nov. 28, 1990 and now abandoned.

BACKGROUND OF THE INVENTION

This invention relates to certain piperidine and pyrrolidine derivatives. The compounds of the invention are muscarinic receptor antagonists which are selective for smooth muscle muscarinic sites over cardiac muscarinic sites and which do not haze any significant antihistaminic activity. Thus the compounds are useful in the treatment of diseases associated with altered motility and/or tone of smooth muscle which can, for example, be found in the gut, trachea and bladder. Such diseases include irritable bowel syndrome, diverticular disease, urinary incontinence, oesophageal achalasia and chronic obstructive airways disease.

South African patent application no. 86/4522 (A. H. Robins Co., Inc.) discloses certain piperidine and pyrrolidine derivatives but these are stated to be useful in treating cardiovascular dysfunctions, countering the effects of histamine in allergies and countering gastric secretion excesses. None of the compounds of the formula (I) set out below are specifically disclosed in the said ZA 86/4522.

SUMMARY OF THE INVENTION

According to the invention there are provided compounds of the formula:

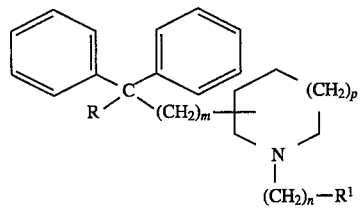
(I)

and their pharmaceutically acceptable salts, wherein

R is —CN or —CONH$_2$;
and
R$^1$ is a group of the formula:

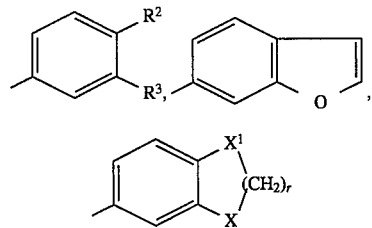

or Het
where

R$^2$ and R$^3$ are each independently H, C$_1$–C$_4$ alkyl, C$_1$–C$_4$ alkoxy, —(CH$_2$)$_q$OH halo, trifluoromethyl, —(CH$_2$)$_q$NR$^4$R$^5$, —SO$_2$NH$_2$, or —(CH$_2$)$_q$CONR$^4$R$^5$;
R$^4$ and R$^5$ are each independently H or C$_1$–C$_4$ alkyl;
q is 0, 1 or 2;
r is 1, 2 or 3;
X and X$^1$ are each independently O or CH$_2$;
m is 1, 2 or 3;
n is 1, 2 or 3, with the proviso that when the group —(CH$_2$)$_m$— is attached to the 3-position of the piperidine or pyrrolidine ring, n is 2 or 3;
p is 0 or 1;
and
"Het" is pyridyl, pyrazinyl or thienyl.

"Halo" means F, Cl, Br or I. Alkyl and alkoxy groups of 3 or carbon atoms can be straight or branched chain. The preferred alkyl and alkoxy groups are methyl, ethyl, methoxy and ethoxy.

m is preferably 1 or 2. R is preferably —CONH$_2$, and p is preferably 1.

R$^1$ is preferably a group of the formula:

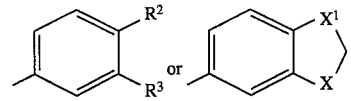

where R$^2$ and R$^3$ are each independently selected from H, halo, and C$_1$–C$_4$ alkyl; and X and X$^1$ are as defined above.

The pharmaceutically acceptable salts of the compounds of formula (I) include acid addition salts such as the hydrochloride, hydrobromide, sulphate or bisulphate, phosphate or hydrogen phosphate, acetate, besylate, citrate, fumarate, gluconate, lactate, maleate, mesylate, succinate and tartrate salts. For a more comprehensive list of pharmaceutically acceptable salts see, for example, the Journal of Pharmaceutical Sciences, Vol. 66, No. 1, January 1977, pages 1–19. These salts can be prepared conventionally, e.g. by mixing a solution of the free base and the acid in a suitable solvent, e.g. ethanol, and recovering the acid addition salt either as a precipitate, or by evaporation of the

DETAILED DESCRIPTION OF THE INVENTION

The compounds of the formula (I) can be prepared by a number of routes, including the following:

Route A

This can be illustrated as follows:

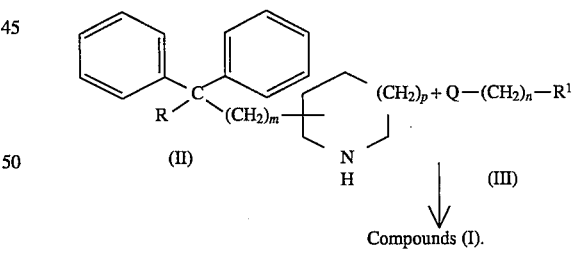

Compounds (I).

m, n, p, R and R$^1$ are as defined for formula (I) and Q is a leaving group, e.g. Br, Cl, I, C$_1$–C$_4$ alkanesulfonyloxy (e.g. methanesulfonyloxy), benzenesulfonyloxy, toluenesulfonyloxy (e.g. p-toluenesulfonyloxy) or trifluoromethanesulfonyloxy. Preferably, Q is Cl or Br.

The reaction is preferably carried out in the presence of an acid acceptor such as sodium or potassium carbonate, sodium hydrogen carbonate, triethylamine or pyridine, and in a suitable organic solvent, e.g. acetonitrile, at up to the reflux temperature. Reaction temperatures of 60°–120° C. are generally desirable and it is most convenient to carry out the reaction under reflux. Iodo is often a particularly suitable leaving group but since the starting materials (III) are most conveniently available as chlorides or bromides the reaction can also be carried out using the compound (III) as a chloride or bromide but in the presence of an iodide such as sodium or potassium iodide. The product (I) can be isolated and purified conventionally.

The starting materials of the formula (II) can be obtained by conventional procedures such as those described in the following Preparations and in ZA 86/4522. The starting materials of the formula (III) are in general known compounds which can be prepared by conventional techniques. The preparation of any novel starting materials of the formula (III) used in the Examples is however described in the following Preparations section.

Route B

The compounds of the formula (I) in which R is —$CONH_2$ can be prepared by the hydrolysis of the corresponding nitriles, e.g. using mineral acid (typically aqueous $H_2SO_4$).

The hydrolysis is typically carried out using concentrated sulphuric acid, preferably 80–98% sulphuric acid and most preferably 90% $H_2SO_4$, with heating at e.g. 80°–110° C. and most preferably at 90°–100° C. The product can then be isolated and purified by conventional procedures.

Route C

This route is useful for preparing compounds in which n is 2 and R is 2- or 4-pyridyl or pyrazinyl and involves the reaction of a compound of the formula (II) with 2- or 4-vinylpyridine or 2-vinylpyrazine.

The reaction is typically carried out with heating, e.g. at about 60° to 110° C. and preferably under reflux, in a suitable organic solvent, e.g. dioxan. In some instances, the use of a basic (preferably a strong base which is soluble in an organic solvent such as N-benzyltrimethylammonium hydroxide ["Triton B"]) or acidic (preferably a $C_1$–$C_4$ alkanoic acid) catalyst may be beneficial.

Route D (For Compounds in Which R is —CN Only)

This involves the following reaction:

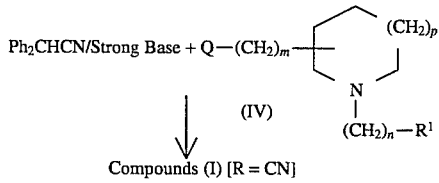

$R^1$, m, n and p are as defined for formula (I) and Q is as defined in Route A.

The preferred strong base is sodium hydride.

The reaction is typically carried out by firstly heating a mixture of diphenylacetonitrile and sodium hydride in a suitable organic solvent, e.g. toluene, under reflux for up to about an hour and then adding the compound (IV) followed by refluxing for a further hour or so, after which time the product (I) can be recovered by conventional techniques.

The starting materials (IV) can be prepared conventionally: typical techniques are described in the following Preparations section.

Route E

This route, which prepares nitriles (IA) in which m is 1 and p is zero, involves a king contraction and can be represented as follows:

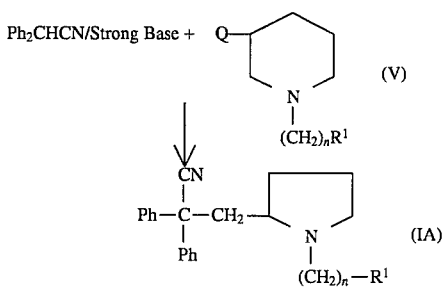

The reaction can be carried out similarly to Route D. n and $R^1$ are as defined for formula (I), and Q is a leaving group (see Route A), preferably Cl.

Route F

This involves the catalytic hydrogenation of a pyridinium bromide of the formula:

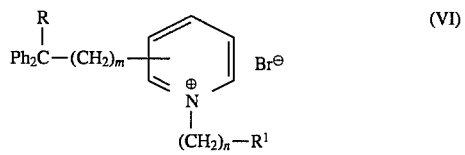

to the corresponding piperidine.

R, $R^1$, m and n are as defined for formula (I).

Noble metal catalysts, particularly platinum oxide, are preferred. The hydrogenation is typically carried out in methanol at about room temperature and under, say, about 1 atmosphere of hydrogen.

The starting materials (VI) are obtainable by conventional techniques such as those illustrated in the following Preparations 4 and 5.

The selectivity of the compounds as muscarinic receptor antagonists can be measured as follows.

Male guinea pigs are sacrificed and the ileum, trachea, bladder and right atrium are removed and suspended in physiological salt solution under a resting tension of 1 g at 32° C. aerated with 95% $O_2$ and 5% $CO_2$. Contractions of the ileum, bladder and trachea are recorded using an isotonic (ileum) or isometric transducer (bladder and trachea). The frequency of contraction of the spontaneously beating right atrium is derived from isometrically recorded contractions.

Dose-response curves to either acetylcholine (ileum) or carbachol (trachea, bladder and right atrium) are determined using a 1–5 minute contact time for each dose of agonist until the maximum response is achieved. The organ bath is drained and refilled with physiological salt solution containing the lowest dose of the test compound. The test compound is allowed to equilibrate with the tissue for 20 minutes and the agonist dose-response curve is repeated until the maximum response is obtained. The organ bath is drained and refilled with physiological salt solution containing the second concentration of test compound and the above procedure is repeated. Typically four concentrations of the test compound are evaluated on each tissue.

The concentration of the test compound which causes a doubling of the agonist concentration required to produce the original response is determined (pA$_2$ value—Arunlakshana and Schild (1959), Brit. J. Pharmacol., 14, 48–58). Using the above analytical techniques, tissue selectivity for muscarinic receptor antagonists is determined.

Activity against agonist induced bronchoconstriction or gut or bladder contractility in comparison with changes in heart rate is determined in the anaesthetised dog. Oral activity is assessed in the conscious dog determining compound effects on, for example, heart rate, pupil diameter and gut motility.

Compound affinity for other cholinergic sites is assessed in the mouse after either intravenous or intraperitoneal administration. Thus, the dose which causes a doubling of pupil size is determined as well as the dose which inhibits the salivation and tremor responses to intravenous oxotremorine by 50%.

For administration to man in the curative or prophylactic treatment of diseases associated with the altered motility and/or tone of smooth muscle, such as irritable bowel syndrome, diverticular disease, urinary incontinence, oesophageal achalasia and chronic obstructive airways disease, oral dosages of the compounds will generally be in the range of from 3.5 to 350 mg daily for an average adult patient (70 kg). Thus for a typical adult patient, individual tablets or capsules will typically contain from 1 to 250 mg of active compound, in a suitable pharmaceutically acceptable vehicle or carrier for administration singly or in multiple doses, once or several times a day. Dosages for intravenous administration will typically be within the range 0.35 to 35 mg per single dose as required. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and such are within the scope of this invention.

For human use, the compounds of the formula (I) can be administered alone, but will generally be administered in admixture with a pharmaceutical carrier selected with regard to the intended route of administration and standard pharmaceutical practice. For example, they may be administered orally in the form of tablets containing such excipients as starch or lactose, or in capsules or ovules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other substances, for example, enough salts or glucose to make the solution isotonic with blood.

In a further aspect the invention provides a pharmaceutical composition comprising a compound of the formula (I), or a pharmaceutically acceptable salt thereof, together with a pharmaceutically acceptable diluent or carrier.

The invention also includes a compound of the formula (I) or a pharmaceutically acceptable salt thereof, for use as a medicament, particularly for use in the treatment of irritable bowel syndrome.

The invention further includes the use of a compound of the formula (I), or of a pharmaceutically acceptable salt thereof, for the manufacture of a medicament for the treatment of diseases associated with the altered motility and/or tone of smooth muscle, such as irritable bowel syndrome, diverticular disease, urinary incontinence, oesophageal achalasia and chronic obstructive airways disease.

The invention yet further includes a method of treatment of a human being to cure or prevent a disease associated with the altered motility and/or tone of smooth muscle, such as irritable bowel syndrome, which comprises treating said human being with an effective amount of a compound of the formula (I), or a pharmaceutically acceptable salt or composition thereof.

The invention also includes any novel starting materials disclosed herein, such as those of the formulae (II), (IV) and (VI).

The following Examples, in which all temperatures are in °C., illustrate the invention:

EXAMPLE 1

4-(2-Carbamoyl-2,2-diphenylethyl)- 1-phenethylpiperidine

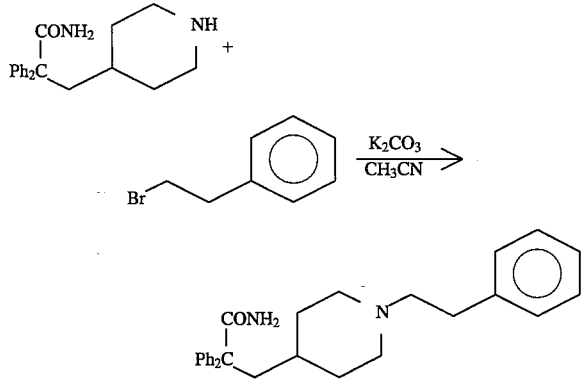

A mixture of 4-(2-carbamoyl-2,2-diphenylethyl)piperidine (300 mg, 0.97 mmol) (Preparation 3), phenethyl bromide (198 mg, 1.07 mmol) and potassium carbonate (400 mg) in acetonitrile (10 ml) was heated under reflux for 6 hours, allowed to cool to room temperature and evaporated. The residue was partitioned between dichloromethane and 10% aqueous potassium carbonate solution and the aqueous layer was extracted twice into dichloromethane. The combined organic layers were dried over magnesium sulphate and evaporated. The residue was purified by chromatography on silica using dichloromethane plus 0–10% methanol as eluant. Appropriate fractions were combined and evaporated to give the title compound (195 mg, 49%) as a colourless foam, which was characterised as a hydrate.

Analysis %: Found: C,78.4; H,7.8; N,6.4; $C_{28}H_{32}N_2O \cdot H_2O$ requires: C,78.1; H,8.0; N,6.5.

EXAMPLES 2–14

The following compounds were prepared by reacting the appropriate (2-carbamoyl-2,2-diphenylethyl)piperidine (Examples 2–11) or 2-(3-carbamoyl-3,3-diphenylpropyl)piperidine (Examples 12–14) with the appropriate alkylating agent as described in Example 1. The alkylating agents are either known compounds or are described in the Preparations, the piperidine starting materials are either known (see e.g. ZA 86/4522) or are described in Preparations 1 and 3, and all the compounds were characterised as the free base in the form indicated.

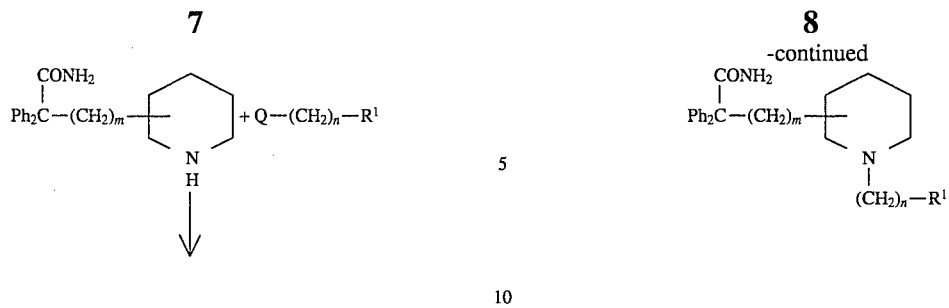

| Example No. | m | n | R¹ | Q | Form Characterised | Positional isomer | Analysis % (Theoretical in brackets) C | H | N |
|---|---|---|---|---|---|---|---|---|---|
| 2 | 1 | 3 | —Ph | Br | foam, dihydrate | 4- | 75.3 (75.3 | 7.8 8.3 | 6.0 6.1) |
| 3 | 1 | 2 | ⟨Ph⟩-Me | Br | foam, hemihydrate | 4- | 79.6 (80.0 | 8.0 8.1 | 6.6 6.4) |
| 4 | 1 | 2 | indanyl | Br | foam, hydrate | 4- | 79.6 (79.1 | 7.9 8.1 | 6.1 5.9) |
| 5 | 1 | 2 | ⟨Ph⟩-Cl | Br | foam, hemihydrate | 4- | 74.2 (74.7 | 7.1 7.1 | 5.9 6.1) |
| 6 | 1 | 2 | benzofuranyl | Br | foam, hemihydrate | 4- | 78.3 (77.7 | 7.8 7.4 | 5.9 6.0) |
| 7 | 1 | 1 | ⟨Ph⟩-Cl | Cl | m.p. 165–167° C. | 4- | 75.0 (74.9 | 6.7 6.7 | 6.6 6.5) |
| 8 | 1 | 2 | —Ph | Br | foam, hemihydrate | 3- | 79.3 (79.8 | 7.8 7.9 | 6.1 6.6) |
| 9 | 1 | 2 | indanyl | Br | foam, hemihydrate | 3- | 80.5 (80.6 | 8.05 8.1 | 5.8 6.1) |
| 10 | 1 | 2 | ⟨Ph⟩-Me | Br | foam, hemihydrate | 3- | 79.8 (80.0 | 8.0 8.1 | 6.3 6.5) |
| 11 | 1 | 2 | ⟨Ph⟩-Cl | Br | foam | 3- | 74.65 (75.2 | 7.0 7.0 | 6.0 6.3) |
| 12 | 2 | 2 | indanyl | Br | gum, 0.67 hydrate | 2- | 80.2 (80.3 | 8.3 8.2 | 5.8 5.9) |
| 13 | 2 | 2 | benzodioxolyl | Br | gum, hydrate | 2- | 73.7 (73.7 | 7.3 7.4 | 5.5 5.7) |

-continued

| Example No. | m | n | R¹ | Form Q | Characterised | Positional isomer | Analysis % (Theoretical in brackets) C H N |
|---|---|---|---|---|---|---|---|
| 14 | 2 | 2 | 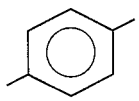 Cl | Br | gum, hemihydrate | 2- | 74.5 7.4 5.8 (74.1 7.3 6.0) |

EXAMPLE 15

2-(2-Carbamoyl-2,2-diphenylethyl)-1-(4-chlorophenethyl)piperidine

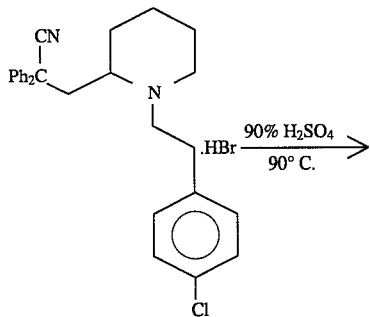

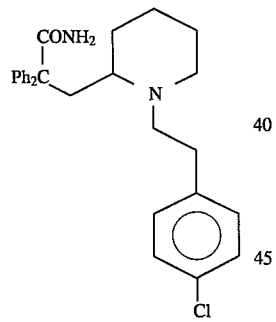

A solution of 1-(4-chlorophenethyl)-2-(2-cyano-2,2-diphenylethyl)piperidine hydrobromide (Example 26) (122 mg, 0.24 mmol) in 90% sulphuric acid (2 ml) was stirred at 90° C. for 1.5 hours, diluted with ice, basified with excess solid potassium carbonate and extracted into dichloromethane. The combined dichloromethane extracts were dried over sodium sulphate and evaporated. The residue was purified by chromatography on silica using dichloromethane plus 0–5% methanol as eluant. Appropriate fractions were combined and evaporated to give the title compound (70 mg, 65%) as a colourless foam which was characterised as a dihydrate.

Analysis %: Found: C,69.8; H,6.5; N,5.7; $C_{28}H_{31}ClN_2O \cdot 2H_2O$ requires: C,69.6; H,6.5; N,5.8.

EXAMPLE 16

(2S)-(2-Carbamoyl-2,2-diphenylethyl)-1-(4-chlorophenethyl)pyrrolidine

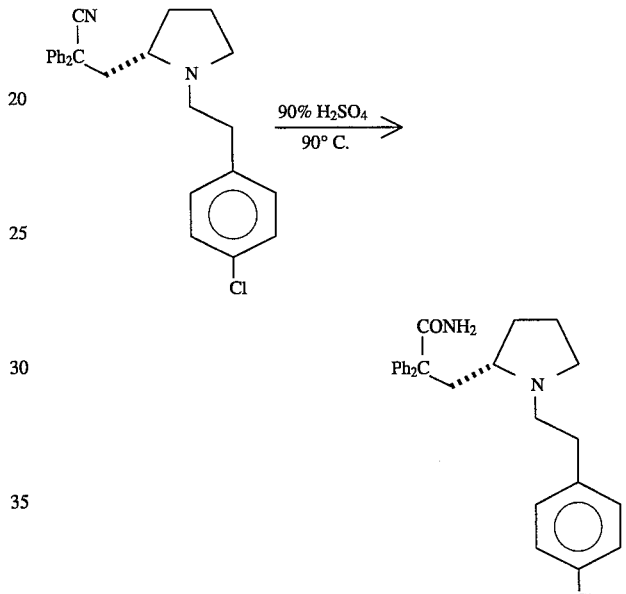

This was prepared as described in Example 15 from 1-(4-chlorophenethyl)-(2S)-(2-cyano-2,2-diphenylethyl)pyrrolidine (see Example 27) instead of 1-(4-chlorophenethyl)-2-(2-cyano-2,2-diphenylethyl)piperidine. The title compound (166 mg, 76%) was obtained as a colourless gum which was characterised as containing 0.25 equivalents of water.

Analysis %: Found: C,74.2; H,6.8; N,6.3; $C_{27}H_{29}ClN_2O \cdot 0.25 H_2O$ requires: C,74.1; H,6.8; N,6.4.

EXAMPLE 17

1-Benzyl-4-(2-carbamoyl-2,2-diphenylethyl)piperidine

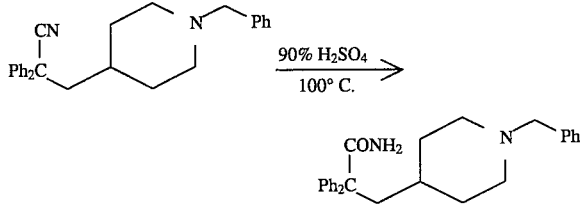

A solution of 1-benzyl-4-(2-cyano-2,2-diphenylethyl)piperidine (7.57 g, 19.9 mmol) (Example 23) in 90% sulphuric acid (45 ml) was heated at 100° C. for one hour, allowed to cool to room temperature, poured into ice, basified with saturated aqueous sodium carbonate solution and extracted into dichloromethane. The combined organic extracts were dried over magnesium sulphate and evaporated. The residue was purified by chromatography on silica using dichloromethane plus 0–10% methanol as eluant. Appropriate fractions were combined and evaporated to give the title compound (1.06 g, 13%) as a colourless foam which was characterised as a hemihydrate.

Analysis %: Found: C,79.5; H,7.6; N,6.8; $C_{27}H_{30}N_2O$ 0.5 $H_2O$ requires: C,79.6; H,7.6; N,6.9.

EXAMPLE 18–21

The following compounds were prepared by reacting 4-(2-cyano-2,2-diphenylethyl)piperidine (see Preparation 13) with the appropriate bromide as described in Example 1.

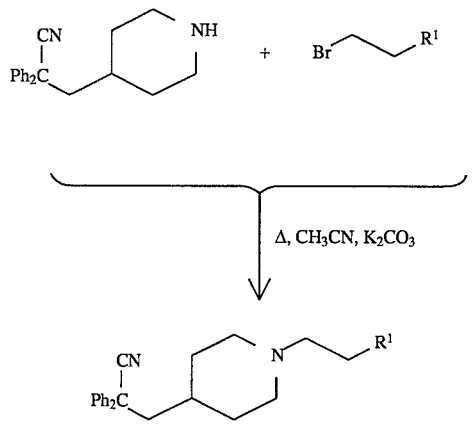

EXAMPLE 22

2-(3-Cyano-3,3-diphenylpropyl)-1-(3,4-methylenedioxyphenethyl)piperidine

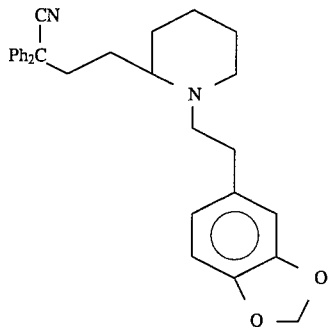

A mixture of 2-(3-cyano-3,3-diphenylpropyl)piperidine (217 mg, 0.74 mmol—see Preparation 18), 3,4-methylenedioxyphenethyl bromide (186 mg, 0.82 mmol—see Preparation 12), potassium carbonate (1.0 g) and sodium iodide (20 mg) in acetonitrile (10 ml) was heated under reflux for 48 hours, allowed to cool to room temperature and diluted with ethyl acetate and water. The organic layer was dried over sodium sulphate and evaporated. The residue was purified by chromatography on silica using dichloromethane plus 0–5% methanol as eluant. Appropriate fractions were combined and evaporated to give the title compound (31 mg, 9%) as a colourless oil, which was characterised as containing 0.75 of an equivalent of water.

Analysis %: Found: C,77.7; H,7.0; N,5.8; $C_{30}H_{32}N_2O_2$.0.75 $H_2O$ requires: C,77.3; H,6.9; N,6.0.

| Example No. | $R^1$ | Melting Point | Analysis % (Theoretical in brackets) | | |
|---|---|---|---|---|---|
| | | | C | H | N |
| 18 | phenyl | 113–114° C. | 85.5 (85.2) | 7.9 7.7 | 7.0 7.1) |
| 19 | 4-chlorophenyl | 106–107° C. | 78.4 (78.1 | 6.8 6.8 | 6.5 6.4) |
| 20 | 2,3-dihydrobenzofuran | 88–97° C. | 82.3 (82.5 | 7.4 7.4 | 6.3 6.2) |
| 21 | 4-methylphenyl | 90–92° C. | 84.7 (85.0 | 7.8 8.1 | 6.8 6.8) |

EXAMPLE 23

1-Benzyl-4-(2-cyano-2,2-diphenylethyl)piperidine

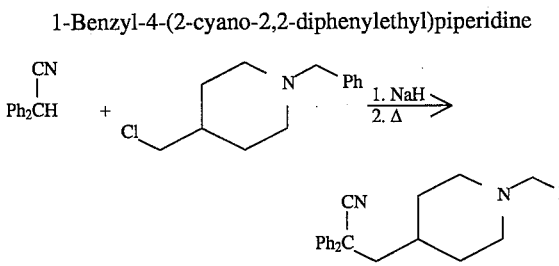

Sodium hydride (1.69 g, 42.1 mmol; 80% dispersion in oil) was added portionwise over 10 minutes to a solution of diphenylacetonitrile (7.4 g, 38.3 mmol) in toluene (40 ml) and the mixture was heated under reflux for 45 minutes, treated with 1-benzyl-4-chloromethylpiperidine (4.3 g, 1.92 mmol; prepared by partitioning the hydrochloride salt, which was obtained by the method described in J. Het. Chem., 1978, 15, 675, between 10% aqueous sodium carbonate solution and dichloromethane, drying the organic layer over magnesium sulphate and evaporating), heated under reflux for one hour, allowed to cool to room temperature and partitioned between toluene and water. The organic layer was dried over magnesium sulphate and evaporated. The residue was purified by chromatography on silica using dichloromethane plus 0–5% methanol as eluant. Appropriate fractions were combined and evaporated to give the title compound (7.57 g, 52%) as a colourless foam which was characterised by its $^1$H-NMR spectrum.

$^1$H-NMR (CDCl$_3$) δ=7.20–7.45 (15 H, m), 3.59 (2H, s), 2.68–2.86 (3H, m) and 1.30–2.47 (8H, m).

EXAMPLE 24

(2R)-(3-Cyano-3,3-diphenylpropyl)-1-[2-(indan-5-yl)ethyl]pyrrolidine

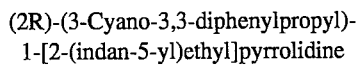
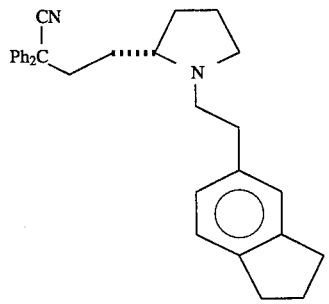

This was prepared as described in Example 23 using (2S)-(2-chloroethyl)-1-[2-(indan-5-yl)ethyl]pyrrolidine (see Preparation 16) instead of 1-benzyl-4-(2-chloromethyl)piperidine. The title compound was obtained as a colourless oil which was characterised as a hemihydrate.

Analysis %: Found: C,84.2; H,7.5; N,6.3; C$_{31}$H$_{34}$N$_2$.0.5 H$_2$O requires: C,83.9: H,7.9; N,6.3.

EXAMPLE 25

1-Benzyl-2-(3-cyano-3,3-diphenylpropyl)piperidine Oxalate

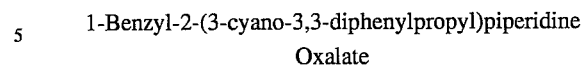
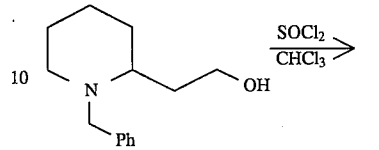
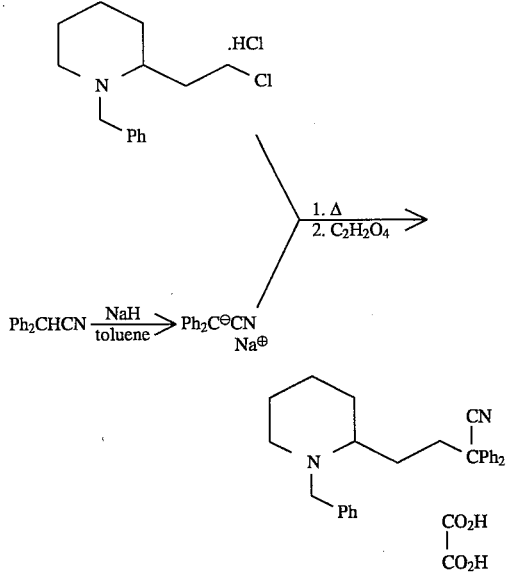

Thionyl chloride (10 ml) was added to a solution of 1-benzyl-2-(2-hydroxyethyl)piperidine (11.64 g, 50 mmol) (Annalen, 1898, 301, 117) in chloroform (150 ml) and the mixture heated under reflux for 45 minutes and evaporated to give crude 1-benzyl-2-(2-chloroethyl)piperidine hydrochloride (16.14 g). A portion of the crude product (6.85 g, 25 mmol) was partitioned between ethyl acetate and 10% aqueous sodium carbonate solution and the organic layer was dried over magnesium sulphate and evaporated. Sodium hydride (2.2 g, 55 mmol; 60% dispersion in oil) was added to a solution of diphenylacetonitrile (9.66 g, 50 mmol) in toluene (100 ml) and the mixture heated at reflux for 1.75 hours, treated with a solution of the above crude residue in toluene (20 ml) and the mixture heated under reflux for 3 hours, allowed to cool to room temperature, washed with water, dried over magnesium sulphate and evaporated. The residue was dissolved in ether and the solution treated with excess ethereal oxalic acid. The resulting precipitate was collected, washed with ether, dried and recrystallised from acetonitrile/ether to give the title compound (5.37 g, 37%) as colourless crystals, m.p. 117°–120° C., which were characterised as a hemihydrate.

Analysis %: Found: C,72.9; H,6.6; N,5.4; C$_{30}$H$_{30}$N$_2$.C$_2$H$_2$O$_4$.0.5 H$_2$O requires: C,73.0; H,6.7; N,5.7.

EXAMPLE 26

1-(4-Chlorophenethyl)-2-(2-cyano-
2,2-diphenylethyl)piperidine Hydrobromide

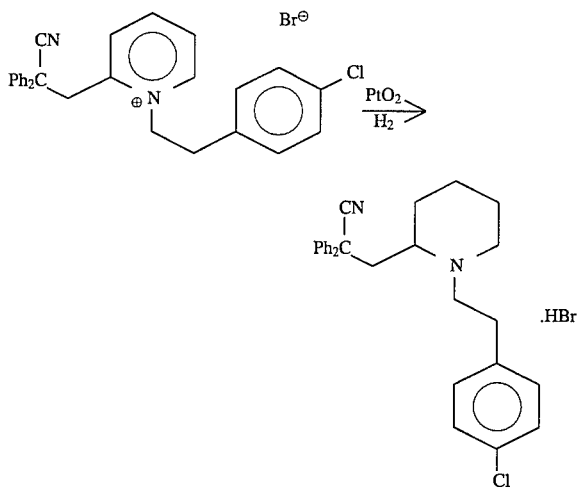

A solution of 1-(4-chlorophenethyl)-2-(2-cyano-2,2-diphenylethyl)pyridinium bromide (252 mg, 0.50 mmol) (see Preparation 4) in methanol (3 ml) was stirred at room temperature under one atmosphere of hydrogen in the presence of platinum oxide (20 mg) for 3 hours, filtered and evaporated to give the title compound (255 mg, 100%) as a colourless foam.

Analysis %: Found: C,65.9; H,6.1; N,5.4; $C_{28}H_{29}ClN_2 \cdot HBr$ requires: C,65.9; H,5.9; N,5.5.

EXAMPLE 27

1-(4-Chlorophenethyl)-(2S)-(2-cyano-
2,2-diphenylethyl)pyrrolidine

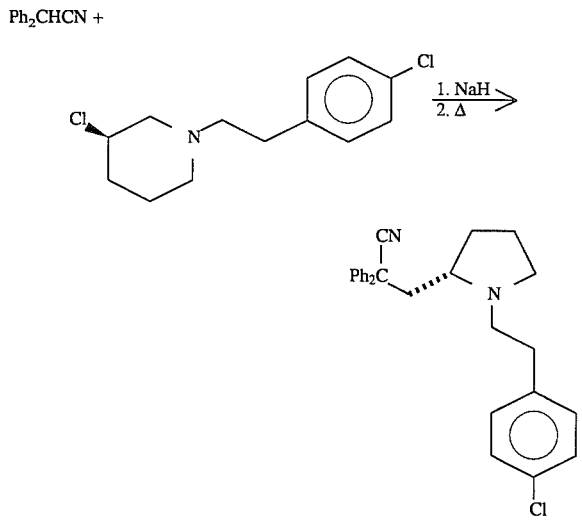

This was prepared by the method described in Example 23 from (3R)-chloro-1-(4-chlorophenethyl)piperidine (see Preparation 6) instead of 1-benzyl-4-chloromethylpiperidine. The title compound was obtained as a colourless gum (330 mg, 16%), $[\alpha]_{589}^{25}$ −36° (c 0.925 in ethanol).

Analysis %: Found: C,78.1; H,6.71; N,6.5; $C_{27}H_{27}ClN_2$ requires: C,78.1; H,6.6; N,6.7.

The following Preparations illustrate the preparation of novel starting materials used in the previous Examples.

PREPARATION 1

2-(3-Carbamoyl-3,3-diphenylpropyl)piperidine
Hydrochloride

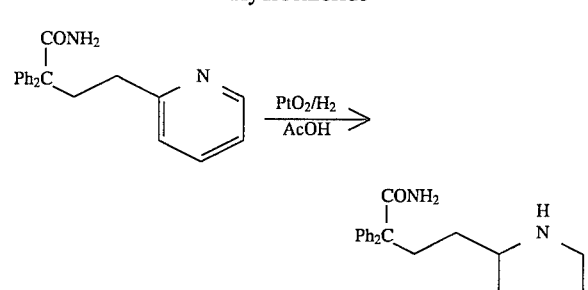

A solution of 2-(3-carbamoyl-3,3-diphenylpropyl)pyridine (3.0 g, 9.5 mmol—see Preparation 2) in acetic acid (80 ml) was stirred at 50° C. under a 50 psi (344.7 kPa) hydrogen atmosphere in the presence of platinum oxide for 3 hours, filtered and evaporated to give the free base of the title compound (3.1 g, 100%) as a colourless oil which was used directly in Examples 12–14. A portion of this oil in ethyl acetate was treated with excess ethereal hydrogen chloride and the resulting precipitate collected, washed with ether, dried and recrystallised from methanol to give the title compound as a colourless powder, m.p. 259°–261° C., which was characterised as containing 0.25 of an equivalent of water.

Analysis %: Found: C 69.5; H,7.8; N 7.7; $C_{21}H_{26}N_2O \cdot HCl \cdot 0.25\ H_2O$ requires: C,69.4; H,7.6; N,7.7.

PREPARATION 2

2-(3-Carbamoyl-3,3-diphenylpropyl)pyridine

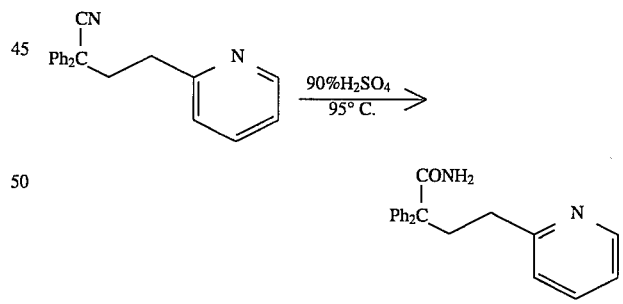

A solution of 2-(3-cyano-3,3-diphenylpropyl)pyridine (5.0 g, 16.8 mmol) (prepared as described in U.S. Pat. No. 2,649,455) in 90% sulphuric acid (10 ml) was heated at 95° C. for 3.5 hours, allowed to cool to room temperature, poured onto ice and basified with 5M aqueous sodium hydroxide solution. The resulting precipitate was collected, washed with water, dried and recrystallised from 2-propanol to give the title compound (4.5 g, 85%) as colourless crystals, m.p. 145°–146° C.

Analysis %: Found: C,79.4; H,6.6; N,8.4; $C_{21}H_{20}N_2O$ requires: C,79.7; H,6.4; N,8.8.

PREPARATION 3

4-(2-Carbamoyl-2,2-diphenylethyl)piperidine

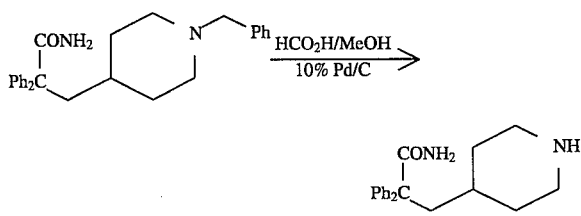

10% Palladium on charcoal (900 mg) was added portionwise over 10 minutes to a stirred, ice-cooled solution of 1-benzyl-4-(2-carbamoyl-2,2-diphenylethyl)piperidine (890 mg, 2.23 mmol) (see Example 17) and formic acid (1.0 ml) in methanol (19 ml) and the mixture stirred at room temperature for 24 hours, filtered and evaporated. The residue was partitioned between dichloromethane and saturated aqueous sodium carbonate solution and the organic layer was dried over magnesium sulphate and evaporated to give the title compound (600 mg, 87%) as a colourless foam which was characterised by its $^1$H-NMR spectrum.

$^1$H-NMR (CDCl$_3$) δ=8.48 (1H, s), 7.20–7.45 (10 H, m), 6.20 and 5.97 (1H, s), 5.56 (1H, s), 3.06–3.40 (3H, m), 2.04–2.72 (4H, m) and 1.20–1.58 (4H, m).

PREPARATION 4

1-(4-Chlorophenethyl)-2-(2-cyano-2,2-diphenylethyl)pyridinium Bromide

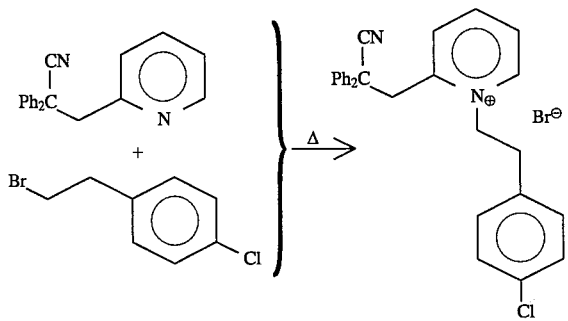

A mixture of 2-(2-cyano-2,2-diphenylethyl)pyridine (1.70 g, 6 mmol) (see Preparation 5) and 4-chlorophenethyl bromide (1.10 g, 5 mmol) was heated at 115° C. for 26 hours, allowed to cool to room temperature and triturated with ethanol:ether=1:2 (15 ml). The resulting solid was collected, washed with ether, dried and recrystallised first from water and then from ether/2-propanol to give the title compound (0.37 g, 14%) as colourless crystals, m.p. 210°–211° C.

Analysis %: Found: C,66.6; H,5.0; N,5.4; C$_{28}$H$_{26}$BrClN$_2$ requires: C,66.7; H,4.8; N,5.6.

PREPARATION 5

2-(2-Cyano-2,2-diphenylethyl)pyridine

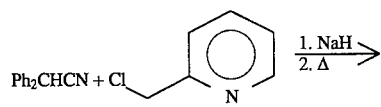

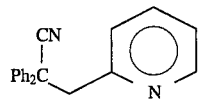

This was prepared by the method described in Example 23 using 2-chloromethylpyridine instead of 1-benzyl-4-chloromethylpiperidine. The title compound was obtained, after recrystallisation from ethyl acetate/hexane, as pale yellow crystals (9.6 g, 68%), m.p. 116°–117° C.

Analysis %: Found: C,84.2; H,5.7; N,10.0; C$_{20}$H$_{16}$N$_2$ requires: C,84.5; H,5.7; N,9.8.

PREPARATION 6

(3R)-Chloro-1-(4-chlorophenethyl)piperidine

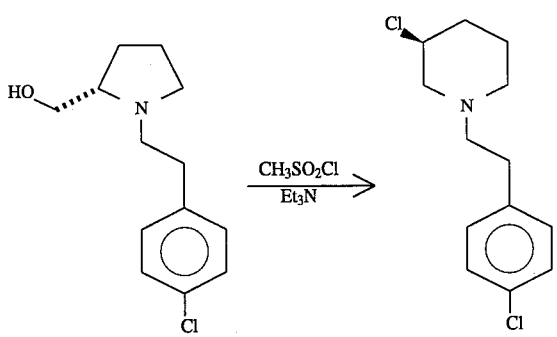

Methanesulphonyl chloride (1.8 ml; 23 mmol) was added to a stirred, ice-cooled solution of 1-(4-chlorophenethyl)-(2S)-hydroxymethylpyrrolidine (5.0 g, 21 mmol) (see Preparation 7) and triethylamine (3.2 ml) in dichloromethane (50 ml) dropwise over 15 minutes and the mixture was stirred at room temperature for 18 hours, washed with 10% aqueous sodium carbonate solution, dried over sodium sulphate and evaporated to give the title compound (4.8 g, 89%) as a colourless oil which was characterised by its $^1$H-NMR spectrum.

$^1$H-NMR (CDCl$_3$) δ=7.28 (2H, d, J=8 Hz), 7.14 (2H, d, J=8 Hz), 3.96–4.07 (1H, m), 3.13 (1H, dd, J=7 and 1.5 Hz), 2.72–2.82 (3H, m), 2.64 (2H, t, J=7 Hz), 2.35 (1H, t, J=8 Hz), 2.10–2.28 (2H, m) and 1.50–1.90 (3H, m).

PREPARATION 7

1-(4-Chlorophenethyl)-(2S)-hydroxymethylpyrrolidine

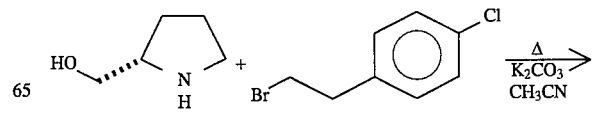

-continued

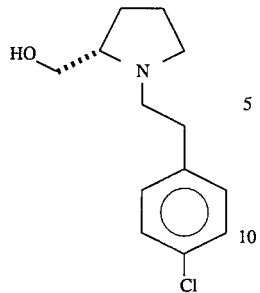

A mixture of pyrrolidine-(2S)-methanol (4.0 g, 40 mmol), 4-chlorophenethyl bromide (9.5 g, 44 mmol) and sodium carbonate (4.6 g) in acetonitrile was heated under reflux for 18 hours and evaporated. The residue was partitioned between ethyl acetate and water and the aqueous layer extracted into ethyl acetate. The combined organic layers were dried over sodium sulphate and evaporated to give the title compound (5.1 g, 53%) as a brown oil which was characterised by its $^1$H-NMR spectrum and which was used in Preparation 6 without further purification.

$^1$H-NMR (CDCl$_3$) δ=7.30 (2H, d, J=8 Hz), 7.12 (2H, d, J=8 Hz), 3.60 (1H, dd, J=7 and 2.5 Hz), 3.37 (1H, dd, J=7 and 1.5 Hz), 3.22–3.32 (1H, m), 2.30–3.05 (7H, m) and 1.65–2.00 (4H, m).

PREPARATION 8

5-(2-Hydroxyethyl)-2,3-dihydrobenzofuran

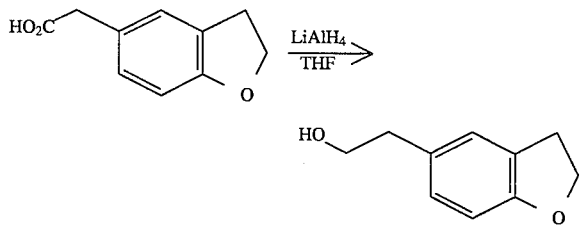

A solution of (2,3-dihydrobenzofuran-5-yl)acetic acid (4.9 g—see EP-A-132130) in anhydrous tetrahydrofuran (50 ml) was added dropwise over 10 minutes to a stirred suspension of lithium aluminium hydride (1.57 g) in anhydrous tetrahydrofuran (50 ml) at 0° C. The mixture was allowed to warm to room temperature and stirred for 1 hour. Water (1.5 ml) was cautiously added dropwise followed by 10% aqueous sodium hydroxide solution (1.5 ml) and water (4.5 ml). The mixture was filtered and the inorganic salts washed with ethyl acetate (2×50 ml). The filtrate and washings were combined and concentrated in vacuo to give the title compound as an oil, yield 3.3 g.

$^1$H-N.m.r. (CDCl$_3$) δ=7.10 (s, 1H); 7.00 (d, 1H); 6.75 (m, 1H); 4.65–4.55 (m, 2H); 3.90–3.75 (m, 2H); 3.30–3.15 (m, 2H); 2.90–2.80 (m, 2H); 1.85–1.75 (brs, 1H) ppm.

PREPARATION 9

5-(2-Bromoethyl)-2,3-dihydrobenzofuran

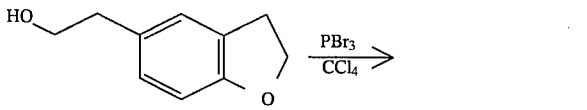

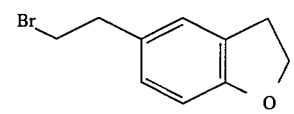

Phosphorus tribromide (0.37 g) was added to a solution of 5-(2-hydroxyethyl)-2,3-dihydrobenzofuran (0.612 g—see Preparation 8) in carbon tetrachloride (3 ml) and the mixture was heated under reflux for 3 hours. On cooling to room temperature, the mixture was partitioned between 10% aqueous sodium carbonate (20 ml) and dichloromethane (20 ml). The layers were separated and the aqueous layer was extracted with dichloromethane (2×10 ml). The combined dichloromethane extracts were dried (MgSO$_4$) and concentrated in vacuo to give the title compound as an oil which crystallised on standing, yield 0.584 g, m.p. 60°–62° C.

$^1$H N.m.r. (CDCl$_3$) δ=7.10 (s, 1H); 7.00–6.95 (d, 1H); 6.80–6.70 (d, 1H); 4.65–4.55 (t, 2H); 3.60–3.50 (t, 2H); 3.25–3.15 (t, 2H); 3.15–3.10 (t, 2H) ppm.

PREPARATION 10

5-(2-Bromoethyl)indane

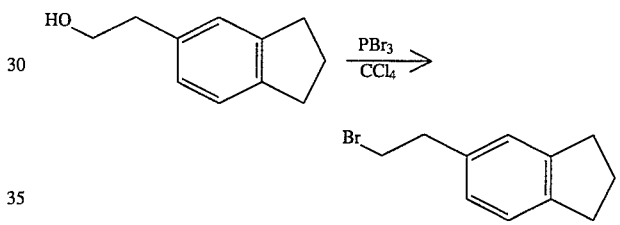

Phosphorus tribromide (3.5 ml) was added, dropwise, to a solution of 5-(2-hydroxyethyl)indane (14.0 g) (FR-A-2139628) in carbon tetrachloride (100 ml). The mixture was stirred at room temperature for 0.5 hour and then heated under reflux for 2 hours. Ice (100 g) was added and the mixture partitioned between dichloromethane and 10% aqueous sodium carbonate. The layers were separated and the aqueous layer extracted with dichloromethane (2×100 ml). The combined dichloromethane extracts were dried (MgSO$_4$) and concentrated in vacuo to give an oil which was purified by column chromatography on silica eluting with dichloromethane. The product-containing fractions were combined and concentrated in vacuo to give the title compound as a colourless oil, yield 10.5 g.

$^1$H N.m.r. (CDCl$_3$) δ=7.30–7.00 (m, 3H); 3.60 (m, 2H); 3.20 (m, 2H); 3.00–2.85 (m, 4H); 2.20–2.05 (m, 2H) ppm.

PREPARATION 11

3,4-Methylenedioxyphenethyl Alcohol

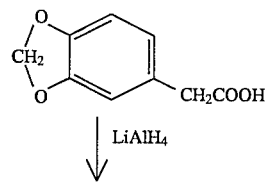

-continued

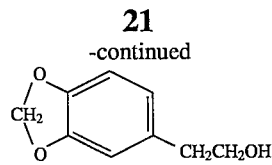

3,4-Methylenedioxyphenylacetic acid (18.0 g) was added portionwise over 30 minutes to a stirred, ice-cooled suspension of lithium aluminium hydride (4.0 g) in ether (400 ml) and the mixture was stirred at room temperature for two hours, quenched by the cautious addition of saturated aqueous ammonium chloride solution and filtered. The filtrate was washed with 10% aqueous sodium carbonate solution, dried over magnesium sulphate and evaporated to give the title compound as a pale yellow oil (15.01 g, 90%), which was characterised by its $^1$H n.m.r. spectrum.

$^1$H N.m.r. (CDCl$_3$) δ=6.69–6.83 (3H, m); 5.98 (2H, s); 3.82 (2H, dt, J=7 and 6 Hz); 2.81 (2H, t, J=7 Hz) and 1.44 (1H, t, J=6 Hz, exchangeable with D$_2$O).

PREPARATION 12

3,4-Methylenedioxyphenethyl Bromide

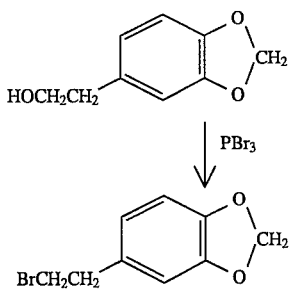

A solution of phosphorus tribromide (8.1 g) in carbon tetrachloride (50 ml) was added dropwise over 30 minutes to a stirred solution of 3,4-methylenedioxyphenethyl alcohol (15.0 g) (see Preparation 11) in carbon tetrachloride (200 ml) and the mixture was heated under reflux for 3 hours, washed sequentially with water (twice), 5M aqueous sodium hydroxide solution and water, dried over magnesium sulphate and evaporated. The residue was purified by chromatogrpahy on silica (100 g) using carbon tetrachloride as the eluant. Appropriate fractions were combined and evaporated to give the title compound as a pale yellow oil (8.3 g, 40%), which was characterised by its $^1$H n.m.r. spectrum.

$^1$H N.m.r. (CDCl$_3$) δ=6.80 (1H, d, J=8 Hz), 6.75 (1H, s); 6.71 (1H, d, J=8 Hz); 6.00 (2H, s); 3.56 (2H, t, J=7 Hz) and 3.13 (2H, t, J=7 Hz).

PREPARATION 13

4-(2-Cyano-2,2-diphenylethyl)piperidine

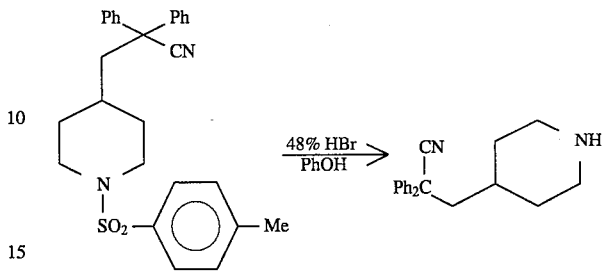

A mixture of 4-(2-cyano-2,2-diphenylethyl)-1-(4-methylphenylsulphonyl)piperidine (20 g, 45 mmol—see Preparation 14) and phenol (20 g) in 48% aqueous hydrobromic acid (200 ml) was heated under reflux for 2 hours, basified with 2M aqueous sodium hydroxide (100 g) cautiously with ice-cooling and extracted into dichloromethane. The organic layer was dried over magnesium sulphate and evaporated. The residue was purified by chromatography on silica using dichloromethane plus 0–10% methanol as eluant. Appropriate fractions were combined and evaporated to give the title compound (10.0 g, 77%) as a colourless powder which was characterised by its $^1$H-NMR spectrum.

$^1$H-NMR (CDCl$_3$): δ=7.25–7.50 (10H, m), 3.76 (1H, q, J=6 Hz), 3.20–3.45 (2H, broad s), 3.09 (2H, d, J=7 Hz), 2.58 (2H, t, J=Hz), 2.40 (2H, d, J=4 Hz), 1.63 (2H, d, J=7 Hz) and 1.20–1.47 (2H, m).

PREPARATION 14

4-(2-Cyano-2,2-diphenylethyl)-
1-(4-methylphenylsulphonyl)piperidine

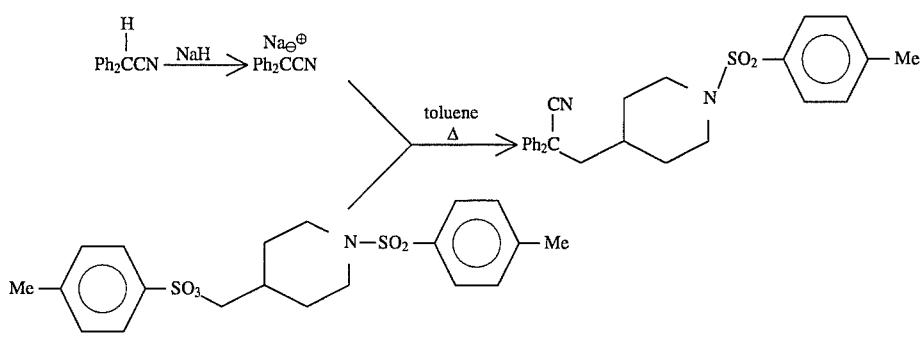

Sodium hydride (3.2 g, 80 mmol; 60% dispersion in oil) was added to a stirred solution of diphenylacetonitrile (13.5 g, 70 mmol) in toluene (200 ml) and the mixture was heated under reflux for 2 hours, treated with a solution of 1-(4-methylphenylsulphonyl)-4-(4-methylphenylsulphonyloxymethyl)piperidine (25.0 g, 60 mmol—see Preparation 15) in toluene (50 ml), heated under reflux for a further 2 hours, allowed to cool to room temperature and diluted with water. The layers were separated and the organic layer was washed with water and saturated brine, dried over magnesium sulphate and evaporated. The residue was crystallised from ethanol to give the title compound (23.0 g, 86%) as colourless crystals, m.p. 130° C.

Analysis %: Found: C,73.0; H,6.4; N,6.3; $C_{27}H_{28}N_2O_2S$ requires: C,72.9; H,6.3; N,6.3.

PREPARATION 15

1-(4-Methylphenylsulphonyl)-4-(4-methylphenylsulphonyloxy)piperidine

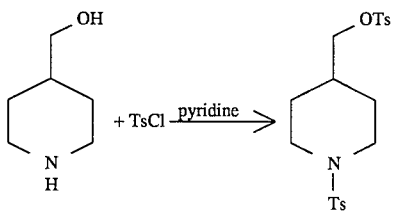

4-Methylphenylsulphonyl chloride (50 g, 0.26 mol) was added portionwise over 10 minutes to an ice-cooled solution of piperidine-4-methanol (15.0 g, 0.13 mol) in pyridine (200 ml) and the mixture was stirred at room temperature for 48 hours and evaporated. The residue was partitioned between dichloromethane and water and the organic layer was washed successively with water, 2M hydrochloric acid and 1% aqueous sodium hydroxide solution, dried over magnesium sulphate and evaporated. The residue was triturated with ether and the resulting solid collected, washed with ether and dried to give the title compound (36 g, 73%) as a colourless solid, m.p. 137°–140° C., which was characterised by its $^1$H-NMR spectrum.

$^1$H-NMR (CDCl$_3$): δ=7.79 (2H, d, J=8 Hz), 7.64 (2H, d, J=8 Hz), 7.37 (2H, d, J=8 Hz), 7.35 (2H, d, J=8 Hz), 3.72–3.92 (4H, m), 2.43 (3H, s), 2.41 (3H, s), 2.20 (2H, dt, J=8 and 1.5 Hz), 1.60–1.82 (3H, m) and 1.21–1.39 (2H, m).

PREPARATION 16

(2S)-(2-Chloroethyl)-1-[2-(indan-5-yl)ethyl]pyrrolidine

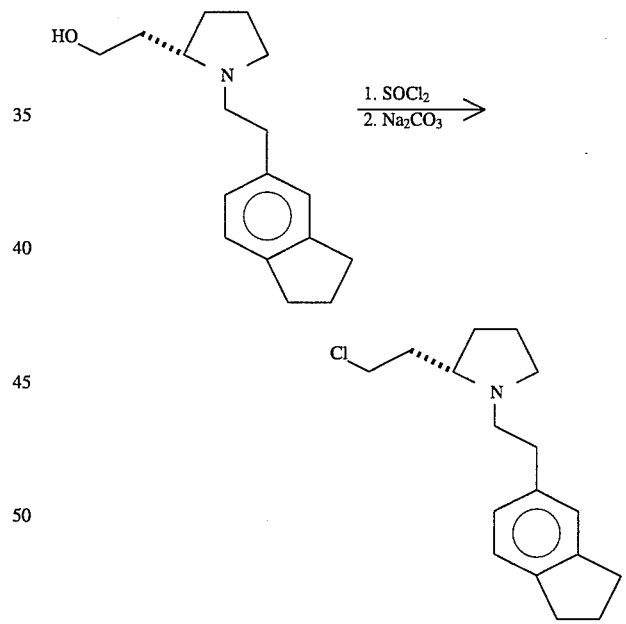

A solution of (2S)-(2-hydroxyethyl)-1-[2-(indan-5-yl)ethyl]pyrrolidine (0.99 g, 3.8 mmol—see Preparation 17) and thionyl chloride (1 ml) in chloroform (15 ml) was heated under reflux for 3 hours and evaporated. The residue was partitioned between ethyl acetate and saturated aqueous sodium carbonate solution and the organic layer was dried over magnesium sulphate and evaporated to give the title compound (956 mg, 91%) as a brown oil which was not characterised before use (Example 24).

PREPARATION 17

(2S)-(2-Hydroxyethyl)-
1-[2-(indan-5-yl)ethyl]pyrrolidine

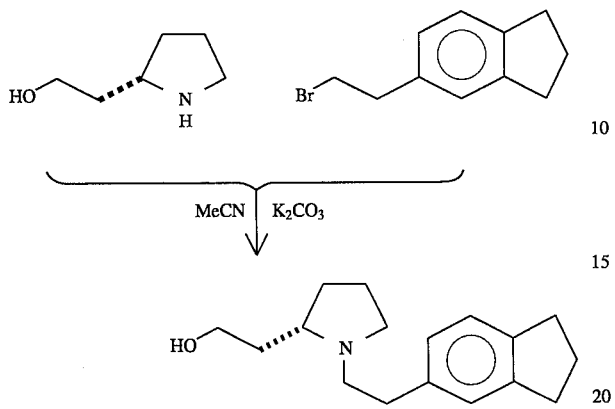

This was prepared as described in Preparation 7 using (2S)-(2-hydroxyethyl)pyrrolidine (Japanese Patent 78/05159; Chem. Abs., 1978, 8–8, 190853e) instead of pyrrolidine-(2S)-methanol. The title compound was obtained as a colourless oil which was characterised by its $^1$H-NMR spectrum.

$^1$H-NMR (CDCl$_3$): δ=7.19 (1H, d, J=8 Hz), 7.13 (1H, s), 7.00 (1H, d, J=8 Hz), 3.97 (1H, dt, J=8 and 2 Hz), 3.61–3.77 (1H, m), 2.60–3.30 (6H, m) and 1.6–2.4 (8H, m).

PREPARATION 18

2-(3-Cyano-3,3-diphenylpropyl)piperidine

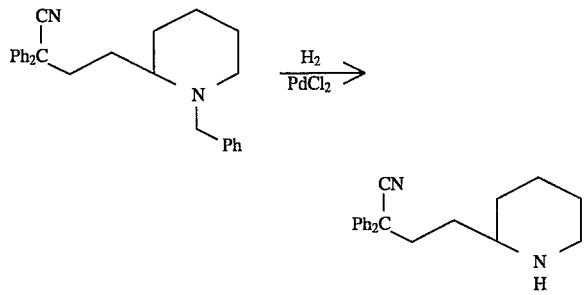

1-Benzyl-2-(3-cyano-3,3-diphenylpropyl)piperidine oxalate (3.70 g, 7.5 mmol—see Example 25) was partitioned between ethyl acetate and 0.5M aqueous sodium hydroxide solution and the organic layer was dried over magnesium sulphate and evaporated. The residue was dissolved in a mixture of acetic acid (5 ml), ethanol (5 ml) and water (2 ml) and the solution treated with sodium acetate (100 mg), palladium dichloride (100 mg) and charcoal. The mixture was stirred under 4 atmospheres of hydrogen at room temperature for 26 hours, filtered and evaporated. The residue was partitioned between ethyl acetate and 10% aqueous sodium carbonate solution and the organic layer was washed with water, dried over magnesium sulphate and evaporated to give the title compound (2.0 g, 88%) as a colourless oil which was characterised by its $^1$H-NMR spectrum.

$^1$H-NMR (CDCl$_3$) δ=7.10–7.50 (10H, m), 3.09 (1H, d, J=7 Hz), 2.30–2.68 (5H, m) and 1.00–1.90 (8H, m).

We claim:
1. A method for treating irritable bowel syndrome in a patient in need of such treatment, characterized by administering to said patient an effective amount of a compound of the formula

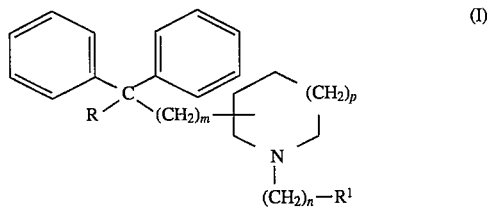

(I)

or a pharmaceutically acceptable salt thereof, wherein

R is —CN or —CONH$_2$; and
R$^1$ is a group of the formula:

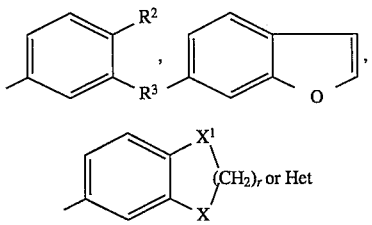

where

R$^2$ and R$^3$ are each independently H, C$_1$–C$_4$ alkyl, C$_1$–C$_4$ alkoxy, —(CH$_2$)$_q$OH, halo, trifluoromethyl, —(CH$_2$)$_q$NR$^4$R$^5$, —SO$_2$NH$_2$, or —(CH$_2$)$_q$CONR$^4$R$^5$;
R$^4$ and R$^5$ are each independently H or C$_1$–C$_4$ alkyl;
q is 0, 1 or 2;
r is 1, 2 or 3;
X and X$^1$ are each independently O or CH$_2$;
m is 1, 2 or 3;
n is 1, 2 or 3, with the proviso that when the group —(CH$_2$)$_m$— is attached to the 3-position of the piperidine or pyrrolidine ring, n is 2 or 3;
p is 0 or 1; and
"Het" is pyridyl, pyrazinyl or thienyl, and a pharmaceutically acceptable diluent or carrier.

2. The method of administration as claimed in claim 1, wherein the compound administered is a compound of the formula (I) wherein m in —(CH$_2$)$_m$— is 1.

3. The method of administration as claimed in claim 2, wherein the compound administered is a compound of the formula (I) wherein R$^1$ is a group of the formula

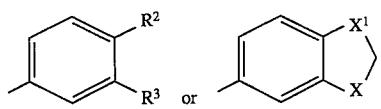

where R$^2$ and R$^3$ are each independently selected from H, halo and C$_1$–C$_4$ alkyl, and X and X$^1$ are each as previously defined.

4. The method of administration as claimed in claim 3, wherein the compound administered is a compound of the formula (I) in which R is —CONH$_2$ and p is 1.

5. The method of administration as claimed in claim 4, wherein the compound administered is a compound of the formula (I), wherein R$^1$ is unsubstituted phenyl, n is 2 and —(CH$_2$)$_m$— is methylene attached to the 4-position of the piperidine ring.

* * * * *